US005507821A

United States Patent [19]
Sennwald et al.

[11] Patent Number: 5,507,821
[45] Date of Patent: Apr. 16, 1996

[54] ARTIFICIAL WRIST JOINT

[75] Inventors: Gontran Sennwald, St. Gallen; Willi Horber, Zürich; Rudolf Koch, Buonas, all of Switzerland

[73] Assignees: Sulzer Medizinaltechnik AG, Winterthur; Allo Pro AG, Baar, both of Switzerland

[21] Appl. No.: 164,121

[22] Filed: Dec. 7, 1993

[30] Foreign Application Priority Data

Jan. 21, 1993 [EP]  European Pat. Off. ............. 93810039

[51] Int. Cl.$^6$ ................. A61F 2/42; A61F 2/30
[52] U.S. Cl. ................................. 623/21; 623/18
[58] Field of Search ................. 623/18, 20, 21, 623/19, 22, 23, 66

[56]  References Cited

U.S. PATENT DOCUMENTS

| | | |
|---|---|---|
| 3,916,451 | 11/1975 | Buechel . |
| 4,040,130 | 8/1977 | Laure ......................................... 623/21 |
| 4,085,466 | 4/1978 | Goodfellow . |
| 4,106,128 | 8/1978 | Greenwald . |
| 4,224,696 | 9/1980 | Murray . |
| 4,259,752 | 4/1981 | Taleisnik . |

FOREIGN PATENT DOCUMENTS

| | | |
|---|---|---|
| 2661817 | 11/1991 | France . |
| 2166654 | 5/1986 | United Kingdom . |
| WO/90/11062 | 10/1990 | WIPO . |

*Primary Examiner*—Debra S. Brittingham
*Attorney, Agent, or Firm*—Townsend and Townsend and Crew

[57]  ABSTRACT

The artificial joint part consists of a distal spherical bearing member (1), which can be attached by attachment means (16) to the capitate bone (14) or/and hamate bone (15), and also of a platform (18), which is attached to the radius (6) and at right angles to the longitudinal axis (7) of the radius (6) towards the ulna (8) comprises a guide surface (5). An intermediate member (2) is supported at the proximal end with a sliding surface (4) on the guide surface (5) and is displaceable in the direction of the ulna (8), whereas at the distal end it forms a spherical bearing (3) for the bearing member (1).

6 Claims, 2 Drawing Sheets

ARTIFICIAL WRIST JOINT

BACKGROUND OF THE INVENTION

The invention relates to an artificial wrist joint enabling flexion and extension movements and distal spherical bearing member with a proximal guide surface attached to the radius and an intermediate member which, at the distal end towards the bearing member, comprises a spherical counter surface and at the proximal end comprises a sliding surface.

An artificial wrist joint is shown in U.S. Pat. No. 4,040,130 in the form of a restricted ball-and-socket joint. There a ball-and-socket joint is connected to several metacarpal bones via a yoke and bone nails. The movement of the ball-and-socket joint is restricted in comparison with an intermediate shell, and the movement of the intermediate shell is restricted in comparison with the bearing shell attached in the radius by grooves disposed so that they intersect one another, in which guide bones slide but cannot twist. The joint permits swivelling about two rigid axes which intersect in the ball-and-socket joint. For a wrist joint the use of such an implant represents great intervention, which is not justified in all disorders of the wrist joint. Especially in arthritic disorders of the wrist joint, when a reduction of the pain takes a priority over a restricted function of the wrist joint, reduced intervention can be an advantage.

SUMMARY OF THE INVENTION

It is an object of the invention to create, with little loss of bone.

The invention has the advantage that it involves less intervention, mainly by removing the scaphoid, lunate and triquetral bones in the proximal carpal row, while the ligaments are extensively retained and after a natural shortening can perform all essential functions. There is also a slight stiffening of the wrist joint by retaining the naturally possible movements between the remaining wrist bones and the metacarpal, while the control of the implanted joint part is dependent on the extension of tendons and ligaments similarly to the natural joint.

The artificial joint part consists of a distal spherical bearing member, which can be attached by attachment means to the capirate bone or/and hamate bone, and a platform, which is attached to the radius and at a right angle to the longitudinal axis of the radius towards the ulna includes a guide surface. An intermediate member is supported at the proximal end with a sliding surface on the guide surface and is displaceable towards the ulna, while at the distal end it forms a spherical bearing for the bearing member. As only a small part of the wrist joint bones is removed, the ligaments are retained and enable good control.

DESCRIPTION OF THE PREFERRED EMBODIMENTS

Figure 1:
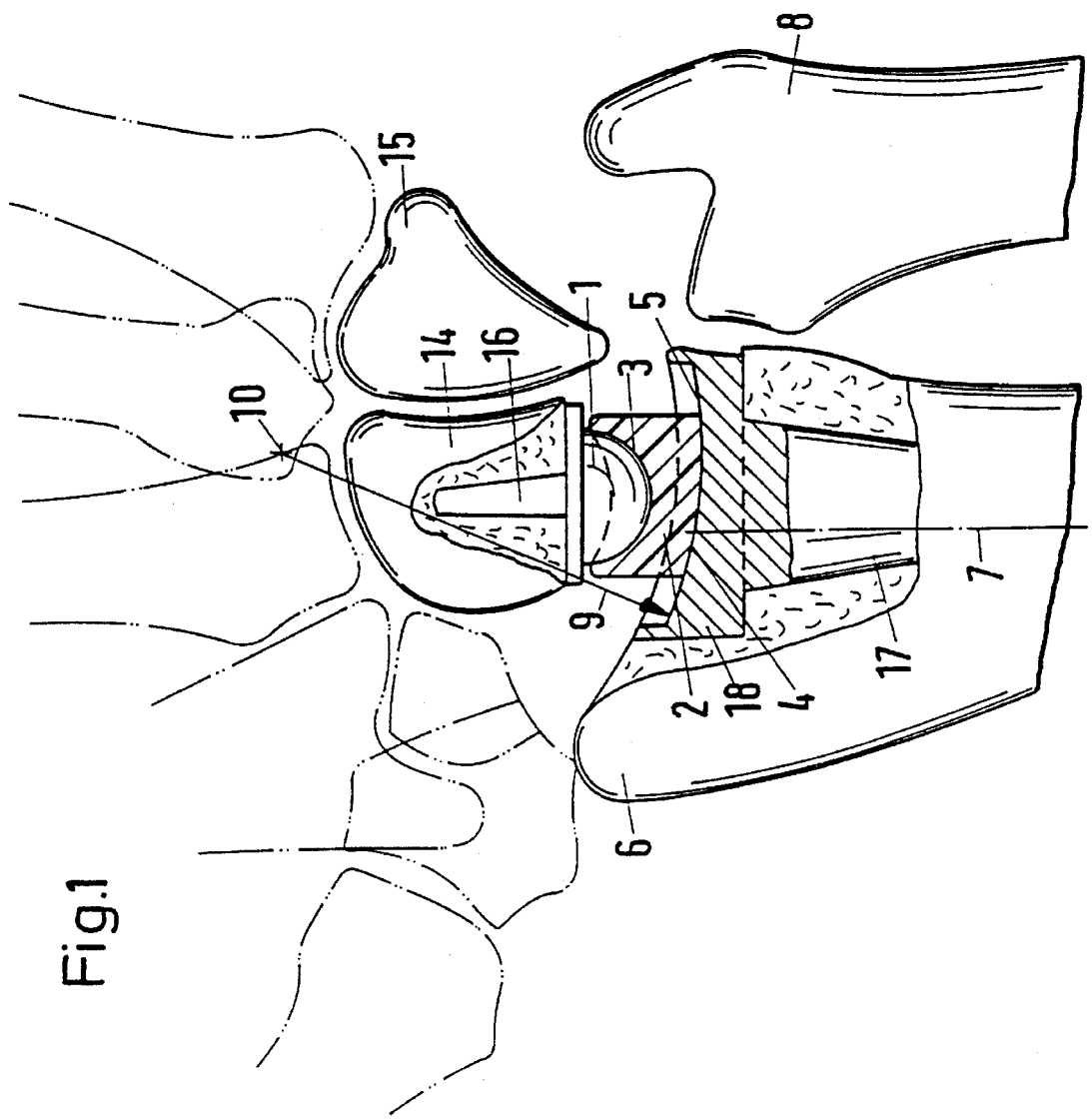
FIG. 1 is a plan view of the enlarged a wrist joint in the plane formed by the radius and ulna.
Figure 2:
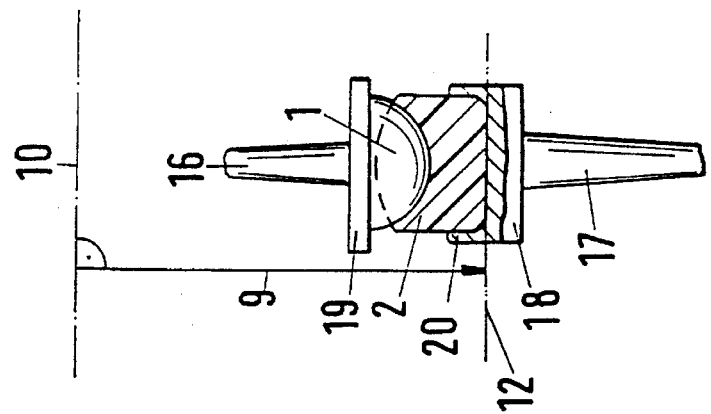
FIG. 2 is a lateral view of the prosthesis parts of the arrangement shown in FIG. 1.

FIGS. 1 and 2 show a wrist joint in which the scaphoid, lunate and triquetral bones have been replaced by an intermediate member 2, which towards the proximal end is supported on a platform 18 having guide surface 5 which is attached to the radius 6 by an attachment 17. The guide surface 5 and collateral guiding surface 20, which limit the platform 18, permit intermediate member 2 to move on its sliding surface 4 at right angles to the longitudinal axis 7 of the radius 6 towards the ulna 8. The sliding surface 4 and guide surface 5 possess a common generatrix 12, which can be rotated about an axis 10, which is perpendicular to the common plane of the radius and ulna. In this case the generatrix 12 is a linear section which can be swivelled with radius 9 about the axis 10. Here the size of the radius 9 is large enough for the axis 10 to be disposed distally outside or beyond the actual joint as shown in FIG. 1.

To the capitate bone 14 is attached a spherical bearing member 1 with a pin 16 at a resection surface. Towards the proximal end the bearing member 1 has a spherical cut-out which is sealed by a protruding collar 19.

A counter-surface 3 in the intermediate member 2 forms a bearing shell, the edge of which in the direction of the flexion/extension movements forms a mean distance to collar 19, which is a multiple of the mean distance in the abduction/adduction direction. The slight clearance between the edge and collar 19 in the abduction/adduction direction ensures that a swivel movement is continued when the collar strikes between sliding surface 4 and guide surface 5, while during a flexion and extension movement swivelling is made possible by the greater distance between the edge and collar 19.

Figure 4:
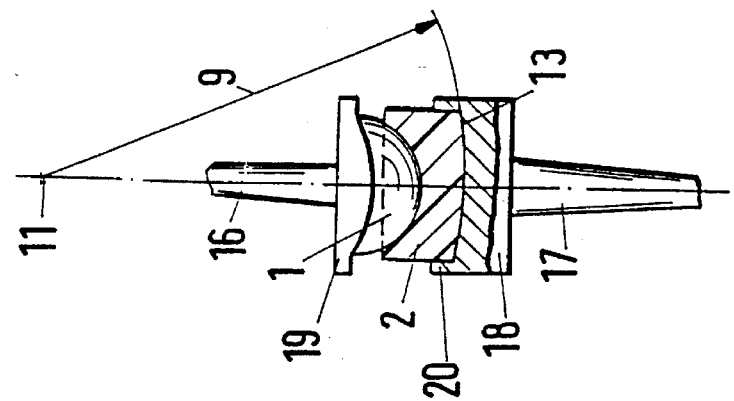
FIG. 4 is a lateral view of the prosthesis parts of the arrangement shown in FIG. 3.
Figure 3:
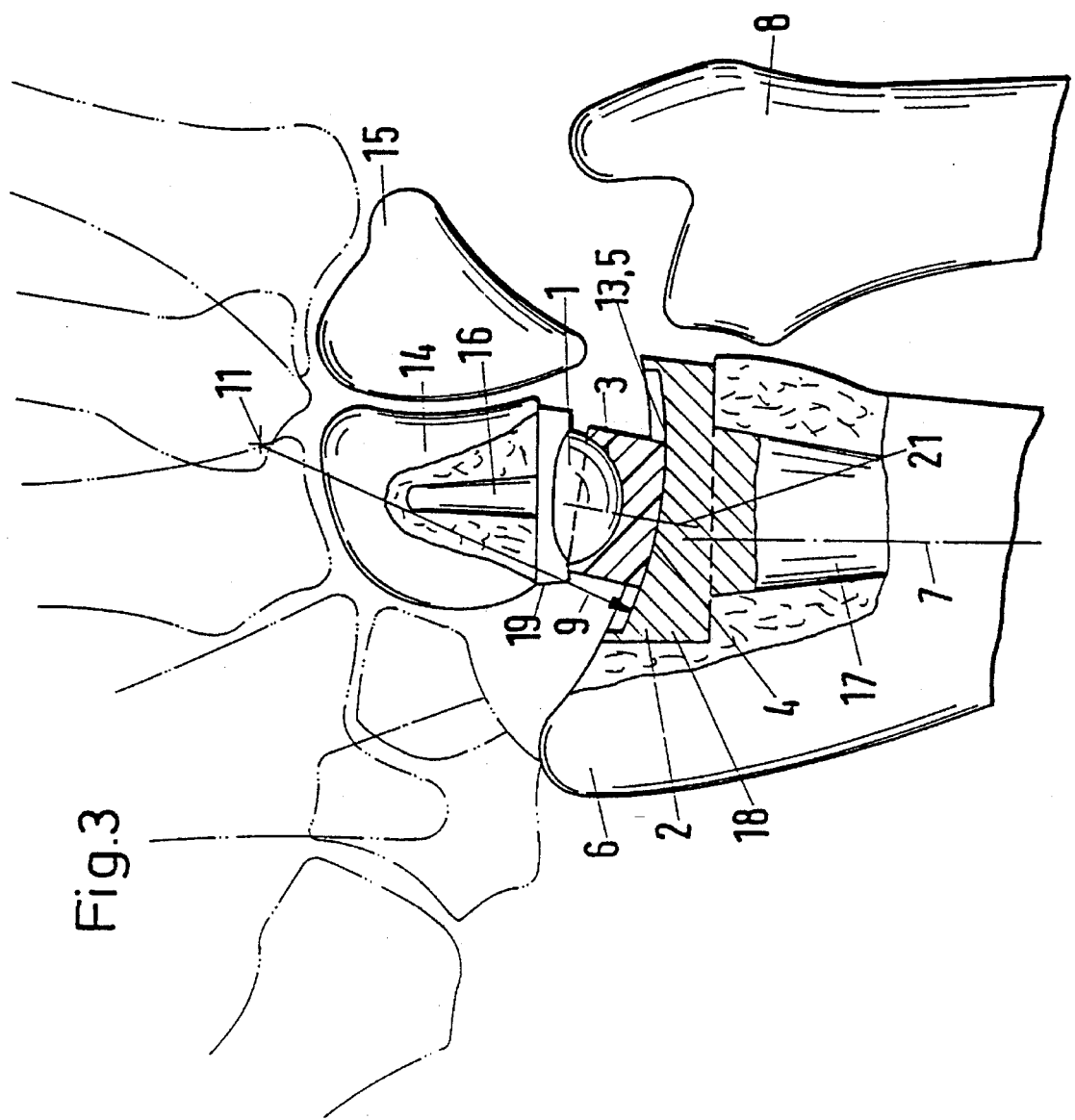
FIG. 3 is a plan view similar to FIG. 1 with an intermediate member rotationally symmetrical to its longitudinal axis.

In FIGS. 3 and 4 in the proximal carpal row the scaphoid, lunate bone and triquetral bone are replaced by an intermediate member 2, which towards the proximal end is supported with a guide surface 4 on a platform 18, which with the sliding surface 4 possesses a common spherical surface 13 as the guide surface 5, the center point 11 of which with radius 9 is disposed beyond the region of the joint towards the distal end. The spherical surface 13 is limited by collateral guiding surface 20 and permits a displacement of the intermediate member 2 at right angles to the longitudinal axis 7 of the radius 6 towards the ulna 8. The intermediate member 2 is designed so that it is rotationally symmetrical with respect to its longitudinal axis 21 and forms a spherical counter-surface 3 to a spherical bearing member 1, which comprises a protruding collar 19 and a pin 16 which is attached to the capitate bone 14. The collar 19 extends further down in the abduction/adduction direction towards the intermediate member 2, to form a displacement stop and provide articulation angle between the collar 19 and the intermediate member 2 in the flexion/extension direction which is a multiple of the articulation angle in the abduction/adduction direction. In FIG. 3 the collar 19 is swivelled to the thumb side to where its downwardly depending portion engages and is stopped by the edge of the intermediate member 2.

As a result of the fact that the capitate bone 14 and the hamate bone 15 are unaltered with respect to the metacarpal indicated by broken lines, the ligaments are extensively retained and as a result there is a mobility which is close to that of the natural joint, while the direct friction points at the bones of the radius and ulna have been relocated to the prosthesis. Inasmuch as the ligaments permit, a limited swivelling of the bearing member 1 about its longitudinal axis is also possible.

What is claimed is:

1. An artificial wrist joint permitting flexion and extension movements comprising a distal spherical bearing member for attachment to at least one of a capitate bone and a hamate bone of a patient, a platform adapted to be attached to a radius bone of the patient, said platform forming a proximal guide surface, an intermediate member for replacing the scaphoid, lunate and triquetral bones in a proximal carpal row of the patient and configured to be disposed between said distal spherical bearing member and said platform, said intermediate member having a distal end facing said bearing member having a spherical counter-surface for engaging said distal spherical bearing member and a proximal end facing said platform said proximal end having a sliding surface for engaging and sliding along said proximal guide surface thereby displacing said sliding surface at right angles to a longitudinal axis of the radius, said proximal guide surface and said sliding surface having a common generatrix with an axis of rotation which is perpendicular to a plane common to the radius bone and the ulna bone of the patient and located beyond the artificial wrist joint in a distal direction.

2. An artificial wrist joint according to claim 1, wherein the platform includes collateral guiding surfaces forming boundaries of said proximal guide surface.

3. An artificial wrist joint according to claim 2 wherein the guide surface and the sliding surface are part of a common spherical surface having a center which is disposed in a plane common to the radius bone and the ulna bone of the patient and located beyond the artificial wrist joint in a distal direction.

4. An artificial wrist joint according to claim 3 wherein the intermediate member has a longitudinal axis and is rotationally symmetrical with respect to said longitudinal axis.

5. An artificial wrist joint according to claim 1, wherein the spherical bearing member comprises a collar forming a displacement stop restricting relative movements between the bearing member and the intermediate member.

6. An artificial wrist joint according to claim 5 wherein the collar and the intermediate member define means permitting articulation therebetween in a flexion/extension direction through an angle of articulation between the guide surface and the sliding surface which is a multiple of an angle of articulation therebetween in an abduction/adduction direction.

* * * * *